(12) United States Patent
Lopatin

(10) Patent No.: US 7,893,603 B2
(45) Date of Patent: Feb. 22, 2011

(54) APPARATUS FOR DETERMINING AND/OR MONITORING A PROCESS VARIABLE

(75) Inventor: Sergej Lopatin, Lörrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 281 days.

(21) Appl. No.: 10/591,607

(22) PCT Filed: Mar. 2, 2005

(86) PCT No.: PCT/EP2005/050905

§ 371 (c)(1),
(2), (4) Date: Jul. 17, 2007

(87) PCT Pub. No.: WO2005/085769

PCT Pub. Date: Sep. 15, 2005

(65) Prior Publication Data

US 2008/0001501 A1    Jan. 3, 2008

(30) Foreign Application Priority Data

Mar. 3, 2004    (DE) .................. 10 2004 010 992

(51) Int. Cl.
*H01L 41/047* (2006.01)
(52) U.S. Cl. .................. 310/369; 310/322; 310/324; 310/359
(58) Field of Classification Search .................. 310/359, 310/369, 322, 324
See application file for complete search history.

(56) References Cited

U.S. PATENT DOCUMENTS

| | | | |
|---|---|---|---|
| 3,745,384 A | 7/1973 | Blanchard | |
| 4,193,010 A | 3/1980 | Kompanek | |
| 4,553,089 A * | 11/1985 | Lewiner et al. | 324/71.1 |
| 5,844,491 A | 12/1998 | Getman | |
| 5,929,554 A * | 7/1999 | Kanayama et al. | 310/359 |
| 6,362,559 B1 * | 3/2002 | Boyd | 310/359 |
| 2003/0159506 A1* | 8/2003 | Brutschin et al. | 73/290 V |
| 2005/0034521 A1* | 2/2005 | Lopatin | 73/649 |

FOREIGN PATENT DOCUMENTS

| | | |
|---|---|---|
| DE | 102 60088 | 8/2004 |
| EP | 087 5740 | 11/1998 |
| EP | 075739 | 11/1998 |
| JP | 60 223300 A | 11/1985 |
| WO | WO/2005/085769 | 9/2005 |

\* cited by examiner

*Primary Examiner*—Walter Benson
*Assistant Examiner*—Bryan P Gordon
(74) *Attorney, Agent, or Firm*—Bacon & Thomas, PLLC

(57) ABSTRACT

An apparatus for determining and/or monitoring a process variable of a medium. The apparatus includes: An oscillatable unit secured on a membrane; a sending/receiving unit, which excites the membrane and the oscillatable unit to oscillate and which receives oscillations of the oscillatable unit. The sending/receiving unit is a disk-shaped, piezoelectric element. The apparatus further includes a control/evaluation unit, which, on the basis of oscillations of the oscillatable unit, monitors and/or determines the process variable. The disk-shaped, piezoelectric element has segments, which are essentially polarized oppositely to one another, and at least two electrodes of opposite polarity are applied to the side of the disk-shaped, piezoelectric element facing away from the membrane.

6 Claims, 3 Drawing Sheets

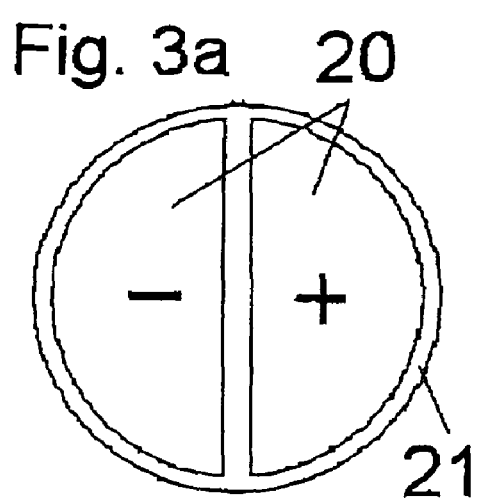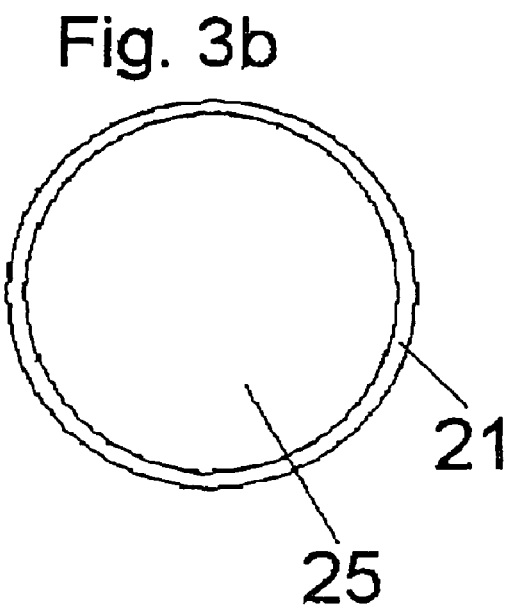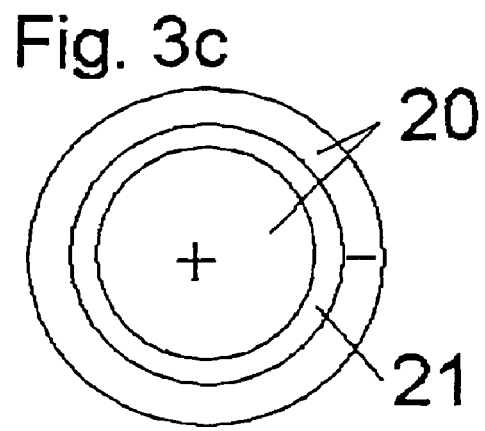

APPARATUS FOR DETERMINING AND/OR MONITORING A PROCESS VARIABLE

FIELD OF THE INVENTION

The invention relates to an apparatus for determining and/or monitoring a process variable of a medium. The apparatus includes an oscillatable unit secured to a membrane, and a sending/receiving unit, which excites the membrane and the oscillatable unit to oscillate and which receives the oscillations of the oscillatable unit, with the sending/receiving unit comprising a disk-shaped, piezoelectric element. The apparatus further includes a control/evaluation unit, which monitors and/or determines the process variable on the basis of the oscillations of the oscillatable unit. The process variable is, for example, the fill level, density or viscosity of a medium.

BACKGROUND OF THE INVENTION

Apparatuses having at least one oscillatory element, so-called vibration detectors, are already known for detecting, or monitoring, the fill level of a fill substance in a container. The oscillatory element is usually at least one oscillatory rod, which is secured to a membrane. The membrane is excited to oscillate via an electromechanical transducer, e.g. a piezoelectric element. Because of the oscillations of the membrane, the oscillatory element secured to the membrane also oscillates.

Vibratory detectors embodied as fill level measuring devices make use of the effect wherein the frequency and amplitude of the oscillations depend on the current degree of covering of the oscillatory element—while the oscillatory element can oscillate in air freely and without damping, it experiences a frequency and amplitude change, as soon as the fill substance rises to cover it partially or completely. On the basis of a predetermined frequency change (usually, the frequency is measured), an unequivocal deduction can then be drawn concerning the reaching of a predetermined fill level of the fill substance in the container. Fill level measuring devices are primarily used as protection against overfilling or for the purpose of protecting against pumps running empty.

The damping of the oscillation of the oscillatory element is also influenced by the present density of the fill substance. Therefore, at constant degree of covering, there is a functional relationship with the density of the fill substance, so that vibration detectors are best suited both for fill level, and also for density, determination. In the practice, for the purposes of monitoring and detecting fill level, or density, of the fill substance in the container, the oscillations of the membrane are registered and converted by means of at least one piezoelement into electrical, received signals. The electrical, received signals are then evaluated by an evaluation electronics. In the case of fill level determination, the evaluation electronics monitors the oscillation frequency and/or the oscillation amplitude of the oscillatory element and signals the state 'sensor covered', or 'sensor uncovered, as soon as the measured values, respectively, fall below, or exceed, a predetermined reference value. A corresponding report to the operating personnel can occur optically or acoustically. Alternatively or supplementally, a switching event is triggered; thus, perhaps, an inlet, or outlet, valve on the container is opened or closed.

DE 100 22 891 discloses an extremely advantageous variant of a sending/receiving unit, via which, on the one hand, the membrane of a vibration detector is excited to oscillate, and via which, on the other hand, the oscillations of the membrane are registered and converted into electrical signals. In each case, two sending and receiving electrodes are provided, which are, essentially, 90°-circular segments and are arranged on the same side of a disk-shaped, piezoelectric element. The piezoelectric element itself is homogeneously polarized and has a circular cross section. An inverter is provided for driving the piezoelectric element.

SUMMARY OF THE INVENTION

An object of the invention is to improve the structure of an apparatus for determining and/or monitoring a process variable in such a manner that the construction and circuit effort is as small as possible.

The object is achieved by the following features: That the disk-shaped piezoelectric element has at least two segments, which are polarized essentially oppositely to one another, and that, on the side of the disk-shaped piezoelectric element facing away from the membrane, at least two electrodes of opposite polarity are applied. The piezoelectric element thus has two segments, which are oppositely polarized to one another. The direction of the polarization should, however, be essentially perpendicular to the membrane. Furthermore, these segments are connected with electrodes, which are of different polarity. A result of this is that the application of an alternating voltage to the electrodes leads in the segments, in each case, alternately, to a shortening and an increasing of the layer thickness of the piezoelectric element. Electrically, the segments are thus connected in series. The great advantage of this is that the piezoelectric element must only be contacted on one side; thus, no electrodes have to be brought to, and connected with, the underside of the piezoelectric element (i.e. to the side of the piezoelectric element facing the membrane). This is, above all, important, when the apparatus has very small dimensions, so that only very little space is present for the running of conductors.

An advantageous embodiment provides that exactly two electrodes of opposite polarity are applied to the side of the disk-shaped piezoelectric element facing away from the membrane. This embodiment is minimal with respect to execution and costs. Associated therewith is the fact that the piezoelectric element only has two segments, which are polarized essentially oppositely to one another. Advantageously, the electrodes are located exactly above the segments and also, in each case, electrically conductively connected only with one segment.

An embodiment includes that the elements are essentially of equal shape. Such a symmetric embodiment has the advantage that a wrong contacting is not possible. Furthermore, in this way, in each case, equally large regions of the piezoelectric element are excited to oscillate.

An embodiment provides that the electrodes have the shape of semicircular segments. This is a special embodiment of the symmetric construction, with this structure also being kept for the application of two electrodes.

An embodiment includes that the electrodes are so structured and arranged that one annularly surrounds the other. This embodiment can also be applied in the case of more electrodes. Preferably, one electrode is a circle (thus it is an annular ring whose radius of the smaller/inner circle is zero) located in the middle of the piezoelectric element and surrounded annularly by the remaining electrode or electrodes.

An embodiment provides that the piezoelectric element is provided on its side facing the membrane, at least partially, with a conductive coating. Additionally, an embodiment includes that the side facing the membrane is connected electrically conductively with ground. In this way, the electric connection of the segments of the piezoelectric element in series is obtained. Depending on the embodiment of the apparatus, the side facing the membrane can also be connected directly conductively with the housing.

BRIEF DESCRIPTION OF THE DRAWINGS

The invention will now be explained in greater detail on the basis of the appended drawings, the figures of which show as follows:

FIGS. 3a, 3b and 3c top views onto the piezoelectric element.

DESCRIPTION OF THE PREFERRED EMBODIMENTS

Figure 1:
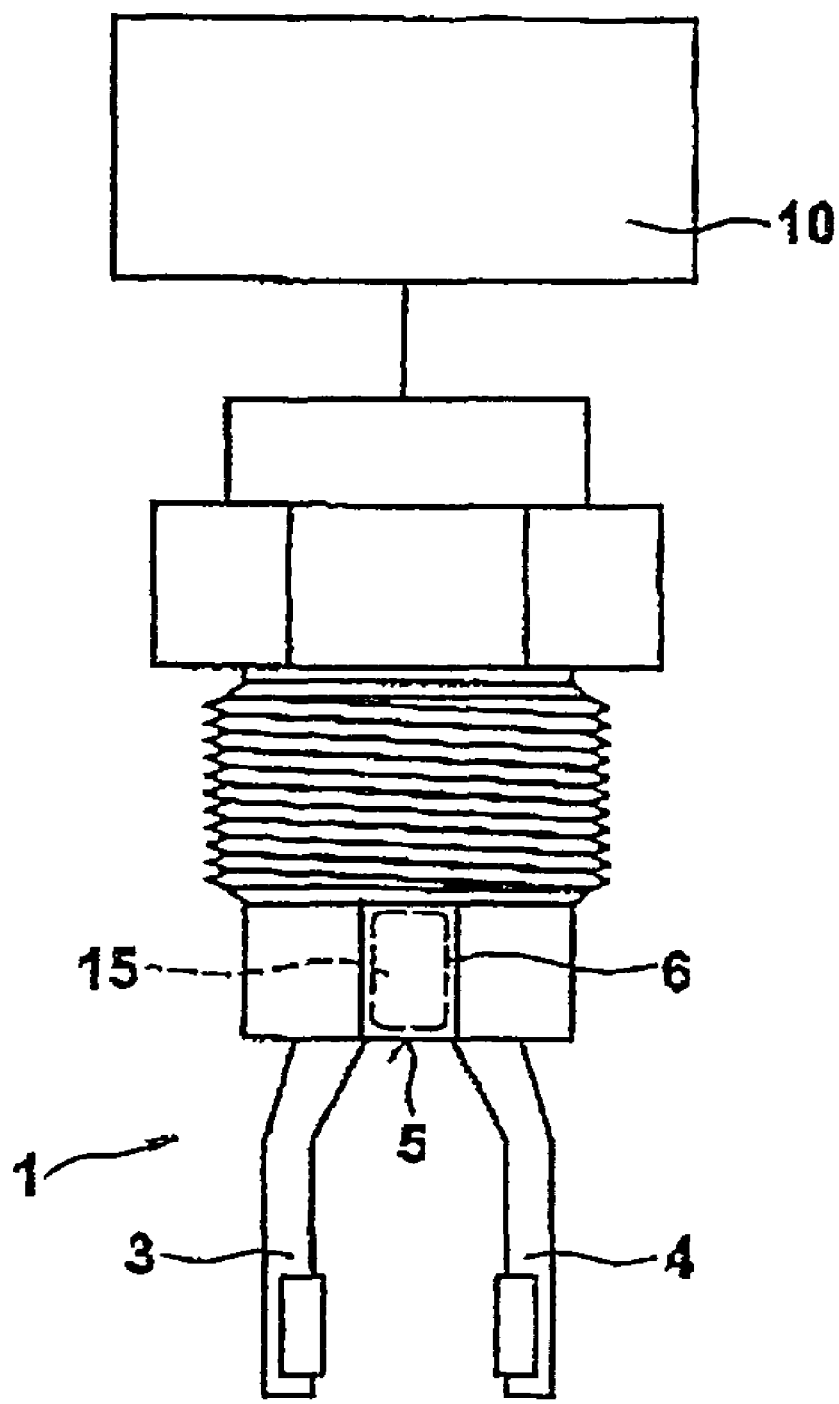
FIG. 1 a schematic drawing of the apparatus of the invention.

FIG. 1 shows a schematic drawing of the apparatus of the invention for determining and/or monitoring a process variable of a medium (not shown) in a container (not shown) The process variable can be the fill level, density or viscosity of the medium. The apparatus has an essentially cylindrical housing. On the lateral surface of the housing, there is a screw thread for securing the apparatus. Secured to a membrane 5 of the apparatus is an oscillatable unit 1 protruding into the container. In the illustrated case, the oscillatable unit 1 is embodied in the form of a tuning fork; thus the tuning fork includes two oscillatory rods 3, 4 secured to the membrane 5 and protruding into the container. A sending/receiving unit 6 causes membrane 5 to oscillate, with the sending unit exciting the membrane 5 to oscillate with a predetermined transmitting frequency and the receiving unit receiving the response signals of the oscillatable unit 1. Due to the oscillations of the membrane 5, the oscillatable unit 1 also oscillates, with the oscillation frequency being different when the oscillatable unit 1 is in contact with the fill substance and a mass-coupling to the fill substance is present, compared with when the oscillatable unit 1 can oscillate freely and without contact with the fill substance.

Piezoelectric elements change their thickness as a function of a voltage difference applied in the direction of polarization. If an alternating voltage is applied, then the thickness oscillates: If the thickness increases, then the diameter of the piezoelectric element decreases; if, on the other hand, the thickness decreases, then the diameter of the piezoelectric element increases correspondingly. Due to this oscillatory behavior of the piezoelectric element 15, the voltage difference effects a flexing of the membrane 5 clamped into the housing. The oscillatory rods of the oscillatable unit 1, since they are arranged on the membrane 5, oscillate with opposite phase about their longitudinal axes, due to the oscillation of the membrane 5. The received electrical signals are evaluated by the control/evaluation unit 10.

Figure 2:
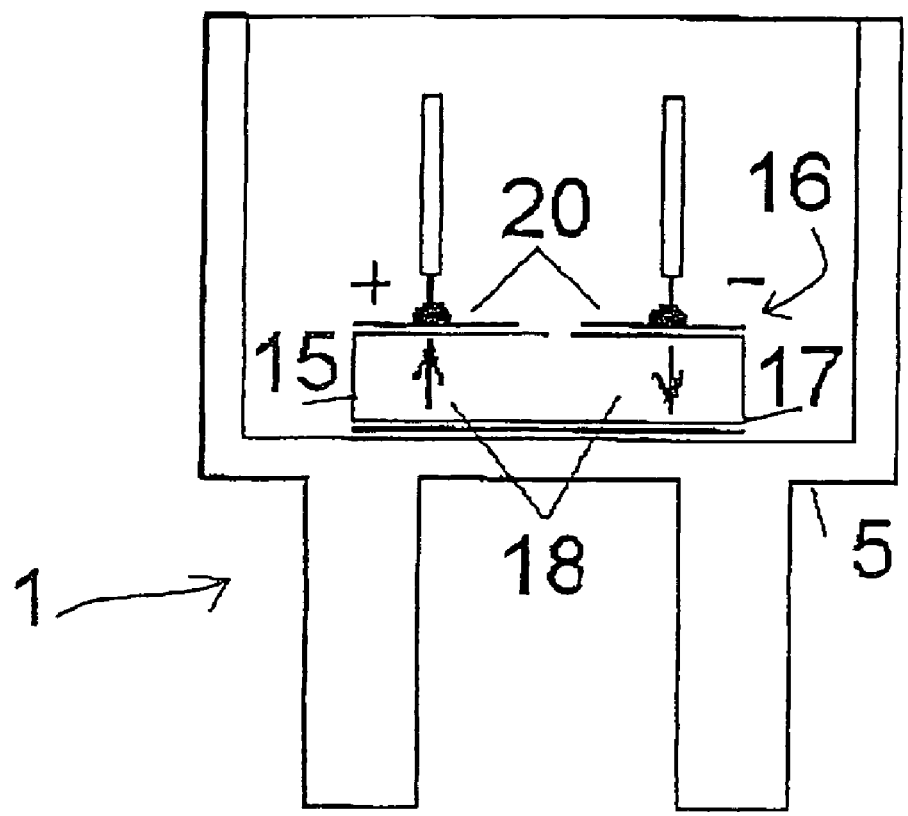
FIG. 2 a section through the apparatus of the invention.

FIG. 2 shows a section through the apparatus. Shown is the piezoelectric element 15 with the segments 18 illustrated here, which are polarized in opposite directions relative to one another (see the arrows indicating the directions of polarization). On top of the segments, on the side of the piezoelectric element 15 facing away from the membrane, are the electrodes 20, which have different polarity (− and +). Due to the different directions of polarization of the segments 18, and the signs of the electrodes 20, an alternating current leads to an alternating thickness change of the piezoelectric element. The side 17 of the piezoelectric element 15 facing toward the membrane can be connected electrically conductively with the housing and, thus, with ground, or, when a galvanic separation is necessary, also an insulating layer can be placed between the piezoelectric element 15 and the membrane 5. For a contacting of the side 17 facing the membrane, it is also possible to contact around a section of the piezoelectric element 15, and, consequently, the connection with ground can be effected via this section.

FIGS. 3a to 3c show two embodiments of the side of the piezoelectric element facing away from the membrane (FIGS. 3a and 3c) and one embodiment of the side facing toward the membrane 5 (FIG. 3b). The piezoelectric element 15 itself is, in each case, preferably circularly shaped. FIG. 3a shows a variant, in which two electrodes 20 are applied, which are essentially semicircularly shaped. Between the electrodes, an insulating layer 21 is applied, so that the electrodes 20 are not short circuited. In FIG. 3c, one electrode 20 is circularly shaped, or this electrode is annularly formed, with its radial thickness being equal to the radius of the outer circle, and the other electrode is annularly formed. Also here an insulating layer 21 is located between the electrodes. FIG. 3b shows the membrane-facing side, which is preferably connected with ground, in order to effect a series connection of the segments of the piezoelectric element. On the membrane-facing side, a conductive layer 25 is applied. For example, layer 25 is of metal. This embodiment of the membrane-facing side can thus be combined with both the variant of FIG. 3a, as well as with that of FIG. 3c, of the other side.

The invention claimed is:

1. An apparatus for determining and/or monitoring a process variable of a medium, comprising:
   a membrane;
   an oscillatable unit secured to said membrane;
   a sending/receiving unit, which excites said oscillatable unit to oscillate and which receives oscillations of said oscillatable unit;
   a control/evaluation unit, which, on the basis of the oscillations of said oscillatable unit, monitors and/or determines the process variable, wherein:
   said sending/receiving unit comprises a disk-shaped, piezoelectric element;
   said disk-shaped, piezoelectric element has two segments, which are essentially polarized oppositely to one another;
   said two segments of said disk-shaped, piezoelectric element are connected in series;
   exactly two electrodes of opposite polarity are applied to the side of said disk-shaped, piezoelectric element; and
   said exactly two electrodes of opposite polarity are applied to said disk-shaped, piezoelectric element facing away from said membrane.

2. The apparatus as claimed in claim 1, wherein:
   said electrodes have essentially the same shape.

3. The apparatus as claimed in claim 2, wherein:
   said electrodes have the shape of semicircular segments.

4. The apparatus as claimed in claim 1, wherein:
   said electrodes are so structured and arranged that they annularly surround themselves.

5. The apparatus as claimed in claim 1, wherein:
   said piezoelectric element is provided on the side facing said membrane at least partially with a conductive coating.

6. The apparatus as claimed in claim 1, wherein:
   the side facing said membrane is connected electrically conductively with ground.

* * * * *